United States Patent [19]

Brindöpke et al.

[11] Patent Number: 4,871,822
[45] Date of Patent: Oct. 3, 1989

[54] REACTION PRODUCT OF OLEFINICALLY UNSATURATED COMPOUNDS WITH COMPOUNDS CONTAINING ACTIVE HYDROGEN, PROCESSES FOR THEIR PREPARATION AND 2-COMPONENT LACQUERS BASED THEREON HOE 85/F 036J

[75] Inventors: Gerhard Brindöpke, Frankfurt am Main; Gerd Walz, Wiesbaden; Karl Waldmann, Bad Soden am Taunus; Manfred Schön, Rodgau; Hans-Jerg Kleiner, Kronberg/Taunus, all of Fed. Rep. of Germany

[73] Assignee: Hoechst AG, Fed. Rep. of Germany

[21] Appl. No.: 874,688

[22] Filed: Jun. 16, 1986

Related U.S. Application Data

[63] Continuation of Ser. No. 718,941, Apr. 2, 1985, abandoned.

[30] Foreign Application Priority Data

Apr. 4, 1984 [DE] Fed. Rep. of Germany ....... 3412658
Mar. 8, 1985 [DE] Fed. Rep. of Germany ....... 3508399

[51] Int. Cl.$^4$ ............................................. C08F 122/04
[52] U.S. Cl. ................................. 526/271; 526/318.2; 526/306
[58] Field of Search ...................... 526/306, 271, 318.2

[56] References Cited

U.S. PATENT DOCUMENTS

| 3,324,017 | 6/1967 | Perry | 526/306 |
| 3,369,007 | 2/1968 | Flodin | 526/306 |
| 3,915,921 | 10/1975 | Schlatzer | 526/318.2 |
| 4,284,732 | 8/1981 | Peterson | 526/271 |
| 4,316,835 | 2/1982 | Gardner | 526/271 |
| 4,330,640 | 5/1982 | Buchwalter | 526/306 |
| 4,408,018 | 10/1983 | Baitman et al. | 525/300 |

*Primary Examiner*—Paul R. Michl
*Assistant Examiner*—Lee C. Wright
*Attorney, Agent, or Firm*—Bierman and Muserlian

[57] ABSTRACT

A reaction product of (A) compounds containing at least two $R^1R^2;C=CR^3$—X groups (I) with (B) compounds which contain
  (a) at least two active H atoms or
  (b) at least two groups containing active H atoms of the type —AH— (II) or
  (c) at least one active H atom and at least one group of the type (III),
or which form the corresponding amount of this group (II), in which the formula (I),
X denotes —CO— which is attached to a further $R^1R^2C=CR^3$ group either directly or via the radical of a polyhydric alcohol or of an amine,
$R^1$ denotes hydrogen or a hydrocarbon radical having 1 to 10, preferably 1 to 4, carbon atoms, such as alkyl, phenyl, benzyl or naphthyl,
$R^2$ denotes hydrogen, a hydrocarbon radical having 1 to 10, preferably 1 to 4, carbon atoms, such as alkyl, phenyl, benzyl or naphthyl, an ester group containing the radical $R^4$ of a monohydric alcohol having up to 12 carbon atoms, —CN, —NO$_2$ or a CO—NHR$^1$ or CO—R$^1$ group, and
$R^3$ has the same meaning as $R^2$ and is identical with or different from the latter, and in formula (II), —AH— denotes one of the grouping —CH—, —NH— and —SH, subject to the proviso that reaction products of (A) polyacrylates containing at least two free acrylic acid groups, reaction products of polyisocyanates with acrylic acid esters containing OH groups or reaction products of epoxy resins, with acrylic acid, with (B) diketene or acetoacetic acid esters of hydroxyethyl acrylate or methacrylate are excluded. In the reaction product, component (A) is a Michael acceptor and component (B) is a Michael donor. The product of the invention has the advantage that it is prepared from components which contain no toxic constituents and can therefore be used without special precautionary measures.

17 Claims, No Drawings

REACTION PRODUCT OF OLEFINICALLY UNSATURATED COMPOUNDS WITH COMPOUNDS CONTAINING ACTIVE HYDROGEN, PROCESSES FOR THEIR PREPARATION AND 2-COMPONENT LACQUERS BASED THEREON HOE 85/F 036J

PRIOR APPLICATION

This application is a continuation of U.S. patent application Ser. No. 718,941 filed Apr. 2, 1985, now abandoned.

It is known to react unsaturated compounds, such as cinnamic acid esters, with H-active compounds, for example malonic acid ester or acetoacetic ester, by a Michael addition reaction with the formation of substituted compounds, for example substituted malonic acid esters (Krauch-Kunz "Namensreaktionen der organischen Chemie" ["Named Reactions of Organic Chemistry"], 5th edition 1976, page 42).

It is also known to use an acrylic resin containing OH groups or an ε-caprolactone-modified acrylic resin mixed with polyisocyanates as two-component lacquers (German Patent Nos. 3,005,945, 3,027,776 and 3,148,022). A further publication describes the reaction of acrylate copolymers containing epoxide groups with a partially masked isocyanate, and the use of the reaction product as a lacquer binder (German Offenlegungsschrift 3,130,545).

The known products have in some cases proved successful. However, attempts have already been made to prepare products more acceptable to the environment by starting from systems not containing free isocyanate.

Thus an acrylic resin which contains oxazolidine and uses water or atmospheric moisture as the curing agent is described in another publication (EP Laid-Open Specification 34,720). This system has the disadvantage that the cured surface resists the deeper penetration of water into the lower layers of the coating and thus prevents complete curing through the whole thickness of the film.

A two-component system which reacts in the absence of isocyanate is also known. This comprises an acrylic resin containing epoxide groups which can be cured by means of another acrylic resin containing tertiary amino groups. In the case of the product prepared by this process, the excessively low degree of crosslinking results in inadequate resistance to chemicals, so that the coatings prepared using this system are only suitable for a limited field of applications.

U.S. Pat. No. 4,408,018 describes acrylic polymers into which acetoacetate groupings have been introduced and which can be crosslinked with α,β-olefinically unsaturated esters in the presence of strong bases via the Michael addition reaction. The introduction of the acetoacetate group is effected via the acetoacetic esters of hydroxymethyl acrylates or methacrylates and subsequent copolymerization with further copolymerizable monomers, or by reacting polymers containing OH groups with the precursor of the acetoacetic ester component, diketene. Polyacrylates containing more than two acrylate groups, reaction products of polyisocyanates with acrylic acid esters containing hydroxyl groups and reaction products of epoxide resins with acrylic acid are mentioned as organic components which can be crosslinked with the polymers containing the acetoacetate groups. These compounds, however, have the disadvantage that the strong bases acting as catalysts, such as alkali metal hydroxides or alcoholates, result in considerable yellowing and cloudiness in the lacquer.

The invention is therefore based on the object of enlarging the supply of lacquer binders available on the market by means of a system which requires no free isocyanates for curing, and is therefore acceptable to the environment. This system employs catalysts which do not shorten the pot life or produce any yellowing in the lacquer film and which produce, with the use of small amounts of catalyst, coatings which meet the high requirements in respect of curing properties and resistance to chemicals.

The present invention therefore relates to a reaction product of (A) compounds containing at least two $R^1R^2C\!=\!CR^3$—X groups (I) with (B) compounds which contain (a) at least two active H atoms or
(b) at least two groups containing active H atoms of the type —AH— (II) or
(c) at least one active H atom and at least one group of the type (II), or which form the corresponding amount of this group (II), in which, in formula (I), X denotes —CO— which is attached to a further $R^1R^2C\!=\!CR^3$ group either directly or via the radical of a polyhydric alcohol or of an amine, $R^1$ denotes hydrogen or a hydrocarbon radical having 1 to 10, preferably 1 to 4, carbon atoms, such as alkyl, phenyl, benzyl or naphthyl, $R^2$ denotes hydrogen, a hydrocarbon radical having 1 to 10, preferably 1 to 4, carbon atoms, such as alkyl, phenyl, benzyl or naphthyl, an ester group containing the radical $R^4$ of a monohydric alcohol having up to 12 carbon atoms, —CN, —NO$_2$ or a CO—NHR$^1$ or CO—R$^1$ group, and $R^3$ has the same meaning as $R^2$ and is identical with or different from the latter, and, in formula (II), —AH— denotes one of the groupings

—NH— and —SH, subject to the proviso that reaction products of (A) polyacrylates containing at least two free acrylic acid groups, reaction products of polyisocyanates with acrylic acid esters containing OH groups or reaction products of epoxy resins with acrylic acid, with (B) diketene or acetoacetic acid esters of hydroxyethyl acrylate or methacrylate are excluded. In the reaction product, component A is a Michael acceptor and component (B) is a Michael donor.

The product according to the invention has the advantage that it is prepared from components which contain no toxic constituents and can therefore be used without special precautionary measures.

Although, in the reaction of compounds (A) containing in each case two groups (I) with compounds (B) containing two active H atoms or two groups (II), even if the latter only contain one H atom, it would be expected, on the basis of the bifunctionality on each side, that a lengthening of the chain would be the sole result, surprisingly, the cured, crosslinked reaction products according to the invention are obtained. The active groups of the compounds (A) and (B) can also be present in a single molecule, so that systems are available which can be cured by intermolecular crosslinking and are self-crosslinking.

If a higher degree of reactivity and thus greater crosslinking of the product is desired, it can be advantageous to employ a procedure such that three or more groups of the type (I) or active H atoms and/or groupings of the type (II) are present in at least one of the compounds (A) and (B).

In one embodiment of the invention the radical $R^1R^2C=CR^3-X$ (I) can be derived from a monounsaturated or polyunsaturated carboxylic acid of a basicity not higher than 2, for example a monocarboxylic and/or dicarboxylic acid having 2 to 10, preferably 3 to 6, carbon atoms, such as cinnamic acid, crotonic acid, citraconic acid or the anhydride thereof, mesaconic acid, fumaric acid, dehydrolevulinic acid or sorbic acid, but preferably acrylic acid, methacrylic acid and/or maleic acid or the anhydride thereof, and can also be derived from unsaturated ketones, such as vinyl ketone or dibenzylacetone; and also from unsaturated nitriles, such as maleic acid mononitrile-monoesters of polyhydric alcohols, from cyanoacrylic acid esters of the formula $H_2C=C(CN)-COOR$, from nitrites of the formula $ROOC-C=CH-NO_2$, from alkylidenemalonic acid esters of the formula $ROOC-C(COOR^4)=CR^1R^2$ or alkylideneacetoacetic estes of the formula $ROOC-C(CO-CH_3)=CR^1R^2$ or the corresponding nitriles, or the like, R in the above formulae being the radical of a polyhydric alcohol and $R^1$ and $R^2$ being hydrogen or alkyl. As a rule, the radicals (I) are present attached in the form of an ester or amide. They can be attached to the radical of a polyhydric alcohol or a compound containing NH groups, such as a polyamine, polyamide or polyiminoamide, or a polyhydric phenol, preferably an oligomer or polymer. Thus the compound (A) can be derived, for example, from saturated and/or unsaturated polyethers or polyesters containing OH groups, for example those based on maleic acid or phthalic acid and diols; acrylic resins containing OH groups; aliphatic, or preferably aromatic, epoxide resins containing, if appropriate, OH groups, for example those based on diphenylolpropane and/or diphenylolmethane, hydantoin and/or amine resins. The radical (I) which is attached in the form of an ester can, for example, have been produced by an addition reaction between acrylic or methacrylic acid and the epoxide group. Examples of polyhydric alcohols which are suitable as starting substances for (A) are alkanediols and alkanetriols, such as ethanediol, the various propanediols, butanediols, hexanediols or octanediols or homologs thereof, the corresponding oligomeric ethers, and also glycerol, trimethylolethane, trimethylolpropane, hexanetriol, pentaerythritol, dipentaerythritol, sorbitol, polyvinyl alcohol or the like.

The following are mentioned as examples of starting compounds, containing NH groups, for the compounds A: alkylenediamines and oligomers thereof, such as ethylenediamine, propylenediamine, butylenediamine, diethylenetriamine, tetramines and higher homologs of these amines, and also aminoalcohols, such as diethanolamine or the like. Aminocarboxylic acid esters of polyhydric alcohols are also examples of suitable amines. Examples of suitable compounds containing NH groups are polyamides of acrylic or methacrylic acid, and also polyurethanes, for example polyisocyanates which have been masked in the form of polyurethane groups, such as those obtained by reacting hydroxyethyl acrylate with polyisocyanates, amine resins, such as methylolmelamines, preferably hexamethylolmelamine, and urea resins, the radical (I) being attached as an amide to the amine groups of these compounds by means of the groupings —CO—. If these amine compounds contain OH groups or alkylol groups, it is also possible for the radical (I) to be directly attached to these resins via an ester group (formula III, see formula sheet) or indirectly via an ether group (formula IV, see formula sheet). It is thus possible to start from a hydroxyalkyl ester or a hydroxyalkyl amide of an unsaturated acid, such as acrylic acid, for the ether linkage of the radical (I). The same applies to a corresponding link to polyhydroxy compounds.

The grouping —AH— (II) in the compound (B) is derived:

(aa) when it denotes

from a compound containing the grouping —CO—CHR$^1$—CO—, NC—CHR$^1$—CO—, NC—CH$_2$—CN, =PO—CHR$^1$—CO—, =PO—CHR$^1$—CN, =PO—CHR$^1$—PO=, or —CO—CHR$^1$—NO$_2$ in which R$^1$ is preferably hydrogen, (bb) when it denotes —NH—, which also embraces NH$_2$, from a primary and/or secondary amine, and (cc) when it denotes —SH, from a thioalcohol acid ester or amide and/or a mercaptan.

$\beta$-Dioxo compounds are preferred.

Examples of suitable compounds (B) of the type (aa) are ketones, such as acetylacetone, benzoylacetone or acetyldibenzoylmethane, and also esters of an optionally alkyl-substituted acetoacetic acid, such as α-methylacetoacetic and/or γ-methylacetoacetic acid, or of acetonedicarboxylic acid, malonic acid units, attached by an ester linkage, of malonic acid and monoalkyl derivatives thereof, linear or branched and having 1 to 6 carbon atoms in the alkyl radical, for example methyl, ethyl and n-butyl, or phenyl, or esters of cyanoacetic acid with monohydric to hexahydric alcohols containing 1 to 10 carbon atoms. The alkyl-substituted esters, for example α-methylacetoacetic esters or α,γ-dimethylacetoacetic esters, contain only one active H atom and are therefore preferably employed in the form of diesters or polyesters of polyhydric alcohols, in order to make available a sufficient number of reactive groups. Examples of alcohols which are suitable for the esterification of the above acids are methanol, ethanol, butanol and octanol and/or, which is preferable, polyhydric alcohols or polyhydroxy compounds such as those mentioned as starting substances for (A). Further examples of compounds (B) are acetoacetic esters, ethanediol bisacetoacetate, glycerol trismalonate, trimethylolpropane, trisacetoacetate, partial esters of these acids with polyhydric alcohols, also the corresponding esters of acrylic resins containing OH groups, polyesters, polyethers, polyester-amides, polyester-imides and polyhydroxylamines, and also nitriles of these acids insofar as these exist, for example malonic acid mononitrile or dinitrile, alkoxycarbonylmethanephosphonic acid esters and the corresponding bismethanephosphonic acid esters (formula VII, see formula sheet). The acids mentioned above can also be attached, in the form of amides, to amines, preferably polyamines, for example to those mentioned above in connection with compound (A), which also embrace oligomers and/or polymers, including amine resins, aliphatic amines being preferred.

Reactive nitro compounds, for example nitroacetic acid derivatives, such as glycerol tris-(nitroacetate) or trimethylolpropane nitroacetate, are also suitable as compounds (aa).

Examples of suitable compounds (bb) are primary and/or secondary polyamines, in particular aliphatic diamines, triamines and higher amines, for example homologs, oligomers and/or polymers thereof, including amine resins, such as have been described earlier in the text, urea and derivatives thereof, and also cyclic polyamines, for example aromatic polyamines, such as phenylenediamine or the like, or mixtures of aliphatic and aromatic amines, it being preferable in this case too to employ aliphatic amines.

Examples of suitable compounds (B) containing a grouping —SH of the type (cc) are thioglycolic, β-mercaptopropionic or thiosalicyclic acid esters of polyhydric alcohols, and thioalcohol ethers and esters, mercaptans, for example ethyl mercaptan and propyl mercaptan and homologs thereof or ethers thereof, for example thioglycerol, and substitution products of cyclic amines with thioalkanols or the like.

Under compounds (B) which form groups of the type (II), examples which should be mentioned are diketene and its α-monoalkyl-substitution products, and also tetrahydrodioxin; these can react with suitable components to form acetoacetic ester or amide groups.

The reaction component (B) can be attached to at least one polyfunctional compound of the group comprising monohydric or polyhydric alcohols, polymers containing OH groups, for example those mentioned earlier in the text, polyamines and polymercaptans, and, in respect of the CH group, is polyfunctional. Thus it can have been prepared, for example, by esterifying a polyepoxide with a carboxylic acid which forms the grouping —AH— (II), for example cyanoacetic acid (equation V, see formula sheet). A component (B) having two active H atoms per epoxide group is obtained in this way. Aromatic or aliphatic polyepoxides, for example those mentioned above, can be employed in this reaction.

If polyamines are used as the starting materials, it is possible to prepare compounds (B) both of the type (aa), in the form of amides, and of the type (bb). If the grouping —AH— has the meaning

, it is possible, for example, to use as starting material 1 mole of an alkylenediamine, which is reacted with 2 moles of acetoacetic ester, with the formation of the compound VI (see formula sheet), which also contains four H atoms activated by amide groups. The polyamines as such are themselves sufficient as compounds (B) in which the group (II) denotes —NH—. For example, it is possible to react 1 mole of trimethylolpropane trisacrylate in this way with 3 moles of ethylenediamine, and the free amine groups in the product can also react with further active acrylate double bonds to produce crosslinking.

The invention also embraces a process for the preparation of reaction products of (A) compounds containing at least two $R^1R^2C=CR^3$—X groups (I) with (B) compounds which contain:

(a) at least two active H atoms or
(b) at least two groups having active H atoms of the type —AH— (II) or
(c) at least one active H atom and at least one group of the type (II), or which form the corresponding amount of this group (II), in which, in formula (I), X denotes —CO— which is attached to a further $R^1R^2C=CR^3$ group either directly or via the radical of a polyhydric alcohol or of an amine, $R^1$ denotes hydrogen or a hydrocarbon radical having 1 to 10 carbon atoms, $R^2$ denotes hydrogen, a hydrocarbon radical having 1 to 10 carbon atoms, an ester group containing the radical $R^4$ of a monohydric alcohol having up to 12 carbon atoms, —CN, —NO$_2$ or CO—NHR$^1$ or CO—R$^1$ group, $R^3$ has the same meaning as $R^2$, and, in formula (II), —AH— denotes one of the groupings

,

—NH— and —SH, which comprises reacting the compounds (A) and (B) with the formation of an oligomeric and/or polymeric reaction product, the reaction being carried out, in the event that —AH— represents one of the groups

or —SH, in the presence of at least one catalyst from the group comprising diazabicyclooctane (DABCO), halides of quaternary ammonium compounds, on their own or as a mixture with alkyl silicates, amidines, organic phosphonium salts having 1 to 20 carbon atoms in the alkyl radical and/or aryl radical, tertiary phosphanes of the general formula $P(CH_2—Y)_3$ in which the Ys are identical or different and denote the radical —OH, CH$_2$CN or —N(Z)$_2$ in which Z is an alkyl radical having 1 to 5 carbon atoms, tertiary phosphanes of the general formula $P(R^4,R^5,R^6)$ in which the radicals $R^4$, $R^5$ and $R^6$ denote an alkyl radical having 1 to 12 carbon atoms or a phenyl radical which is unsubstituted or substituted by at least one alkyl, alkoxy or dialkylamino group each of which has 1 to 4 carbon atoms in the alkyl radical, and $R^4$, $R^5$ and $R^6$ are identical or different, but at least one of the radicals represents a phenyl radical, and aminophosphoranes of the general formula $(R^7,R^8,R^9)P=N—C(R^{10},R^{11},R^{12})$ in which $R^7$, $R^8$ and $R^9$ are identical or different and denote an alkyl radical having 1 to 12 carbon atoms or a phenyl radical which is unsubstituted or substituted by at least one alkyl, alkoxy or dialkylamino group each of which has 1 to 4 carbon atoms in the alkyl radical, and $R^{10}$, $R^{11}$ and $R^{12}$ are identical or different and each represents an alkyl radical having 1-5 carbon atoms or a phenyl radical.

The invention also embraces a process for the preparation of the reaction products mentioned in claim 1, the reaction being effected, in the event that —AH— represents one of the groups

or —SH, in the presence of at least one quaternary ammonium compound or an alkali metal alcoholate as a catalyst.

These processes take place very smoothly. Since the starting materials used are preferably oligomeric and/or polymeric compounds A and B, oligomeric and/or polymeric reaction products are also obtained. In general, the reaction is carried out at −10° to 180°, preferably 0° to 100° and especially 20° to 80° C. For example, products of good hardness are obtained at room temperature after 2 to 24 hours or at 60° C. after 10 to 40 minutes.

The reaction of compounds (B) in which the grouping (II) is —NH— or —NH$_2$ can be carried out in the absence of a catalyst. On the other hand, one or more catalysts are used, as a rule, if the grouping —AH— represents a

group (the preferred form) or an —SH group. Examples of catalysts suitable for the Michael addition reaction are those belonging to the group comprising diazabicyclooctane (DABCO), halides of quaternary ammonium compounds, such as alkylammonium, arylammonium and/or benzylammonium bromide, chlorides and, in particular, fluorides, the halides being optionally employed in combination with alkyl silicates in order to improve the activity of the catalyst further. Specific examples which should be mentioned are alkylbenzyldimethylammonium halides (alkyl=C$_{16}$-C$_{22}$), benzyltrimethylammonium halides and tetrabutylammonium halides, in each case especially the fluorides, and also copolymerized triphenylvinylphosphonium fluoride. Further suitable catalysts are the organic phosphonium salts, corresponding to the above ammonium halides and having 1 to 20 carbon atoms in the alkyl radical and/or aryl radical, for example trimethylbenzylphosphonium halides, tributylhexadecylphosphonium bromide, amidines, such as tetramethylguanidine, diazabicycloundecene, diazabicyclononene and others.

Further suitable catalysts for the process for the preparation of Michael adducts are the phosphanes (formerly known as phosphines), for example (a) tertiary phosphanes P(CH$_2$—Y)$_3$, such as tris-2-cyanoethylphosphane, trisdiethylaminomethylphosphane, preferably trishydroxymethylphosphane and trisdimethylaminomethylphosphane, (b) tertiary phosphanes P(R$^4$, R$^5$, R$^6$), such as triphenylphosphane, tris-p-tolylphosphane, tris-o-anisylphosphane, tris-p-dimethylaminophenylphosphane, phenyldi-p-anisylphosphane, phenyldi-o-anisylphosphane, diphenyl-p-anisylphosphane, diphenyl-o-anisylphosphane, diphenyl-p-dimethylaminophenylphosphane, butyldiphenylphosphane, methylditolylphosphane, ethyldi-p-anisylphosphane, (diethylaminomethyl)-diphenylphosphane, preferably tris-p-anisylphosphane, methyldiphenylphosphane and methyldi-p-anisylphosphane, and (c) iminophosphoranes (R$^7$, R$^8$, R$^9$) P=N—C (R$^{10}$, R$^{11}$, R$^{12}$), such as α,α-dimethylbenzylimino-tris-(dimethylamino)-phosphorane, α,α-dimethylbenzyliminomethyldiphenylphosphorane, t.-butyliminotriphenylphosphorane or preferably α,α-dimethylbenzyliminotributylphosphorane.

Examples of catalysts for the Michael addition reaction which can also be employed for the preparation of specific reaction products are those belonging to the group comprising alkali metal alcoholates, such as lithium butylate, sodium methylate or potassium methylate, or quaternary ammonium compounds, such as alkylammonium, arylammonium and/or benzylammonium hydroxides or carbonates. Specific examples which may be mentioned are alkylbenzyldimethylammonium hydroxide (alkyl=C$_{16}$-C$_{22}$), benzyltrimethylammonium hydroxide and tetrabutylammonium hydroxide. The catalysts or catalyst mixtures mentioned can be used in the presence of tertiary aliphatic amines which in themselves are not active at room temperature, such as, for example, triethylamine, N-methyldiethanolamine, N-methyldiisopropanolamine or N-butyldiethanolamine. These auxiliaries can be present in an amount of 0.1–5, preferably 0.1–1% by weight.

The amount of catalyst is, in general, 0.01 to 5, preferably 0.02 to 2% by weight, relative to the total solids content of the starting material. It can be varied depending on the reactivity of the compounds (A) and (B) and the intended mode of carrying out the process. The catalyst can also be added in portions, i.e. in several stages.

In one embodiment of the invention, the compounds (A) are reacted as a mixture containing a minor proportion of compounds (A) which contain only one group of the formula I, or the compounds (B) are reacted as a mixture containing a minor proportion of compounds (B) which contain only one active H atom or only one group of the formula (II). This alternative will, however, only be made use of if it is desired to reduce the density of crosslinking and to vary the associated properties of the product correspondingly. This is particularly the case when at least one of the components (A) and (B) effects a particularly high degree of crosslinking, as the result of a relatively high proportion of reactive groups, for example if a monomolecular hexaacrylic acid ester is used, so that an undesirable stiffening of the reaction product, and hence the risk of possible embrittlement, must be expected in a given case. In this embodiment, the proportion of compounds containing only one group (I) or (II) will not be more than 20, preferably not more than 10 and particularly up to 5% by weight, relative to the particular analogous compound (A) or (B). By making an addition of this type it is possible to control the hardness and elasticity of the reaction product to a certain extent. Examples of compounds (A) containing only one reactive group (I) which should be employed for this variant are the esters or amines of the unsaturated carboxylic acids which have been enumerated for (A), but which have been esterified, or reacted with the formation of amides, only with monohydric alcohols or monoamines.

Examples of compounds (B) which are suitable for this embodiment are those containing the groupings mentioned above under (aa) in which R$^1$ has a meaning other than hydrogen, for example the alkyl-substitution products of acetoacetic acid and malonic acid which have been esterified only with a monohydric alcohol or reacted only with a monoamine. Compounds (B) of the type (bb) are amines having only one active H atom on the amino group, such as secondary monoamines, for example diethylamine, and those of type (cc) are alkanol-mercaptans containing only one mercaptan group, for example ethyl mercaptan.

The process according to the invention can be carried out in one or more stages. As a rule, however, for reasons of economy of labor, the single-stage process will be preferred, for example by carrying out the reaction with equivalent proportions of components containing in each case two active groups or H atoms (equation XII, see formula sheet and underlined H atoms). The choice of process stages and of the pot life and properties of the product therefore depends on the process conditions, i.e. on the nature and amount of the starting materials, the metering in of the catalyst and the temperature profile. Thus, the elasticity of the crosslinked product can be controlled within a tolerance range, for example by means of the chain length of the oligomers and/or polymers employed for (A) or (B).

Although the process according to the invention is operated discontinuously as a rule, it is also within the scope of the invention to carrying out the mixing of the components and the progress of the reaction continuously, for example by means of an automatic lacquering device.

If the process is carried out in several stages, one or more of the components can be added in portions. For example, in the first stage 1 mole of butanediol bisacrylate can be reacted with 2 moles of malonic acid diamide (equation XI, see formula sheet), with the formation of a product containing two groups (II) each of which has an active (underlined) H atom. This product can be reacted in at least one further stage with further molecules of a compound (A), with lengthening of the chain and crosslinking. Analogously, it is possible, for example, to react one mole of trimethylolpropane trisacrylate or trismethacrylate in the first stage with three moles of acetylacetone.

The crosslinking in the second stage and, if appropriate, further subsequent stages, can be effected, for example, by the addition of a catalyst. The procedure employed can be such that the reaction in the first stage is carried out with only a relatively small amount of catalyst, for example less than 2%, or with a catalyst of relatively low activity. If the second or subsequent stages are carried out relatively soon after the preparation of the precursor, it is not necessary to remove the catalyst which may have been employed in the first stage. Either a higher dose of the same catalyst and/or another catalyst can be used in the second stage. It is also possible to prepare, in the first stage, a precursor which is stable on storage for a prolonged period of time and can thus be despatched to the processor. In this case, it will be advantageous to remove the catalyst, for example by neutralization or distillation, or to employ a catalyst which is either attached from the outset to a polymer, such as polymerized triphenylvinylphosphonium fluoride, or which becomes attached to a polymer during the reaction. Before ultimate application, the crosslinking reaction will be set in progress by a further addition of an adequate amount of catalyst.

The process according to the invention can be carried out in the presence or absence of organic solvents which, in a given case, also exert an effect on the activity of the catalysts. Examples of suitable solvents are aromatic and aliphatic hydrocarbons, such as toluene, the various xylenes, mixtures of aliphatic and/or aromatic hydrocarbons, mineral oil fractions, esters, ethers, alcohols or the like.

All the reactants can be employed on their own or as a mixture, insofar as they are compatible with one another.

Although the process according to the invention is usually carried out under normal pressure, it can be desirable in individual cases also to work under an elevated pressure in order to increase the rate of curing.

The ratio of the amounts of reactants (A) and (B) to one another depends on the number of unsaturated groups (I) in compounds (A) and the sum of the active H atoms in compound (B), that is to say including those in the groups (II) (referred to in brief below as "active double bonds: active H atoms"). If the process is carried out in several stages, this ratio can be varied within a wide range for the preparation of the precursors. For the preparation of the crosslinked end product, however, the said ratio of active double bonds:active H atoms is generally about 2.4:0.8 to 0.8:2.4, preferably about 2:1 to 1:2 and particularly about (0.8 to 1.2):1 to 1:(0.8 to 1.2). Therefore, because of the two active H atoms in the acetoacetic ester, only about 0.8 to 1.2 moles of acetoacetic ester will, for example be used for one mole of ethanediol bisacrylate. If, on the other hand, it is desired to react only one H atom in the acetoacetic ester, it is also possible to employ $2 \times (0.8$ to $1.2)$ moles of acetoacetic ester (formula XII, see formula sheet). As can be seen from this formula, the reaction product still contains one reactive group (see the underlined H atom), so that it can crosslink further either with other molecules or with itself. The ratio of active double bonds:active H atoms is then 1:1. On the other hand, it is also possible to employ a mixture of the components A on the one hand and/or B on the other hand, with a different functionality in each case, in order to control the degree of crosslinking in the end products.

The reaction mixture according to the invention is a 2-component system which exhibits pot lives varying between 5 minutes and about 12 hours, depending on the choice of the compounds (A) and (B) and on the nature and amount of the catalyst or combination of catalysts. This ensures a high degree of reliability in processing. Because of this advantageous property of the product, in conjunction with its rapid and fault-free curing at room temperature or elevated temperatures and its resistance to chemicals, it is excellently suitable for use as a binder for coatings.

The 2-component systems can be applied as coatings to many kinds of substrates, for example to substrates of an organic or inorganic nature, such as wood, wood fiber materials, for example for sealing wood, textiles of natural or synthetic origin, plastics, glass, ceramics, building materials, such as concrete, fiberboards or artificial stone, but particularly to metal. The coatings can also be employed for domestic and industrial articles and equipment, for example refrigeration equipment, washing machines, electrical equipment, windows, doors, furniture or the like. The preferred use is, however, for motor vehicles. Application can be carried out by brushing, spraying, dipping or electrostatic means. The 2-component systems can, of course, also contain the customary additives, such as dyestuffs, pigments, fillers, plasticizers, stabilizers, leveling agents, neutralizing substances, such as tertiary amines, and catalysts, and these can be used in the customary amounts. These substances can be added to the individual components and/or to the total mixture.

The following are mentioned as examples of dyestuffs or pigments, which can have an inorganic or organic nature: titanium dioxide, graphite, carbon black, zinc chromate, strontium chromate, barium chromate, lead chromate, lead cyanamide, lead silicochromate, calcium molybdate, manganese phosphate, zinc oxide, cadmium sulfide, chromic oxide, zinc sulfide, nickel titanium yellow, chromium titanium yellow, red oxide of iron, black oxide of iron, ultramarine blue, phthalocyanine complexes, naphthol red or the like.

Examples of suitable fillers are talc, mica, kaolin, chalk, powdered quartz, powdered asbestos, powdered slate, barium sulfate, various grades of silica, silicates or the like.

The customary solvents are used for the fillers, for example aliphatic and aromatic hydrocarbons, ethers, esters, glycol ethers and esters thereof, ketones, chlorinated hydrocarbons, terpene derivatives, such as toluene or xylene, ethyl acetate, butyl acetate, ethylene glycol monoethyl ether-acetate, ethylene glycol monobutyl ether-acetate, ethylene glycol dimethyl ether, diethylene glycol dimethyl ether, cyclohexanone, methyl ethyl ketone, acetone, isophorone or mixtures thereof.

The scope of the invention therefore also includes 2-component systems which are suitable for the production of coatings, preferably motor vehicle lacquers and especially automobile refinishing paints. The resistance to xylene and hence, at the same time, good resistance to premium grade gasoline is of particular interest in this respect. The use, according to the invention, of the reaction products is therefore particularly advantageous. Since the 2-component system in accordance with a preferred embodiment of the invention can cure of itself at room temperature within a relatively short time, without environmentally polluting substances being liberated, its use as an automobile refinishing paint is of considerable practical importance.

In the instructions and Examples below, % denotes in each case % by weight and parts denote in each case parts by weight. Vacuum is to be understood in each case as meaning a waterpump vacuum.

EXAMPLES

I

Preparation of the component A (Michael acceptor)

(A1) 400 parts of acrylic acid, 200 parts of toluene, 3 parts of hydroquinone monomethyl ether and 3 parts of p-toluenesulfonic acid were added to 400 parts of a solvent-free acrylic resin (®Macrynal SM 510 made by Hoescht AG) (OH No. 150). The mixture was heated under a water separator, while air was passed through it, until the evolution of H$_2$O was complete. After the mixture had been cooled to room temperature and washed with water, the excess acrylic acid was removed. The organic phase was freed from the solvent by vacuum distillation and was diluted to a solids content of 60%. C=C equivalent weight 864.

(A2) 500 parts of methyl acrylate, 3 parts of hydroquinone monomethyl ether and 6 parts of dibutyltin oxide were added to 510 parts of the acrylic resin mentioned under A1. 26 parts of methanol were distilled off through a Vigreaux column at an internal temperature of 80° to 90° C. in the course of 30 hours. The excess methyl acrylate was removed by vacuum distillation. The residue was diluted with xylene to a solids content of 60%. C=C equivalent weight 1,083.

(A3) 1,000 parts of an acrylic resin containing glycidyl groups, prepared from styrene, glycidyl methacrylate and dimethyl maleate (epoxide equivalent weight 510) were dissolved in 660 parts of xylene at 70° C. 127 parts of acrylic acid and 1 part of tetraethylammonium bromide were added at 70° C. The mixture was subsequently stirred at 80° C., while air was passed through it, until an acid number of 1 was reached. The pale yellow solution was diluted with 17 parts of xylene. Solids content 62.5%, C=C equivalent weight 1,022.

(A4) 0.1 part of dibutyltin diluarate and 50 parts of n-butyl isocyanate were added to 570 parts of the resin solution from Example A3. The mixture was subsequently stirred for 4 hours at 60° C. (NCO value 0.2%). Solids content 65%; C=C equivalent weight 1,112.

(A5) 296 parts of trimethylolpropane trisacrylate were initially placed in a 1 l flask equipped with a stirrer, a reflux condenser and a gas inlet, and 200 parts of isopropanol and 1.5 parts of triethylamine were added. 17 parts of hydrogen sulfide were absorbed at room temperature. The mixture was stirred for a further hour at 30° C. The heavier product phase formed was then separated off as a nearly colorless liquid. Solids content 88%; C=C equivalent weight 172.

(A6) 657 parts of a melamine resin of the hexamethoxymethyl melamine type (molecular weight 399), 1,053 parts of 2-hydroxyethyl acrylate, 3.3 parts of hydroquinone monomethyl ether and 1.65 parts of sulfuric acid were initially placed in a three-necked flask equipped with a stirrer, a thermometer and a distillation column fitted with a descending condenser. The mixture was warmed to 75° C. in vacuo and was heated at 95° C. for 4 hours. After being cooled to room temperature, it was neutralized with 10 parts of a 10% strength methanolic potassium hydroxide solution and filtered. This gave 141 parts of a clear resin solution of low viscosity. C=C equivalent weight 175.

(A7) 1 part of dibutyltin dilaurate was added to 220 parts of isophorone diisocyanate, and the mixture was warmed to 50° C. 2 parts of hydroquinone monomethyl ether, dissolved in 232 parts of hydroxyethyl acrylate, were added dropwise in the course of one hour at the same temperature. The mixture was then stirred until the N=C=O content was less than 0.5. After 7 parts of a glycidyl ester of a saturated G$_{9-11}$ fatty acid, branched in the α-position, (episode equivalent weight 260) and 0.5 part of chromium-III octoate had been added, the mixture was stirred for 5 hours at 80° C., and 115 parts of xylene were then added. Solids content 80%; C=C equivalent weight 289.

II

Preparation of the component B (Michael donor)

(B1) 312 parts of neopentylglycol and 706 parts of methyl acetoacetate were heated to 130° to 160° C. under N$_2$ as a protective gas in a 2 l glass flask, equipped with a distillation bridge, a stirrer and an electrical thermometer. When the removal of methanol by distillation was complete (after approx. 7 hours), the mixture was cooled to 120° C. The excess methyl acetoacetate was removed by vacuum distillation. This left a residue of 819 parts of a clear, pale liquid. C—H equivalent weight 70.

(B2) 670 parts of trimethylolpropane and 1,972 parts of methyl acetoacetate were heated from 130° to 180° C. in the course of 5 hours in a 4 l apparatus analogous to that of B1. When the distillation was complete, the receiver contained 465 parts of methanol. The mixture was cooled to 150° C., and the low-boiling fraction was removed by vacuum distillation. This left a residue of 1,950 parts of a colorless liquid. C—H equivalent weight 64.

(B3) 335 parts of trimethylolpropane and 2,400 parts of diethyl malonate were heated to 150° to 170° C. under $N_2$ as a protective gas in the same apparatus as that of B1. When the removal of the ethanol by distillation was complete, the excess diethyl malonate was removed by vacuum distillation at 150° to 160° C. This left a residue of 1,201 parts of a colorless liquid. C—H equivalent weight 79.

(B4) 92 parts of glycerol and 426 parts of 2,2,6-trimethyl-4-oxo-4H-1,3-dioxin were initially placed in an apparatus as described in B1. 160 parts of acetone were removed by distillation at 180° C., with stirring, in the course of 5 hours. The residue was then freed from low-boiling constituents at 120° C. in vacuo. This left 348 parts of a yellow liquid of low viscosity. C—H equivalent weight 58.

(B5) 300 parts of ethyl acetoacetate, 3 parts of potassium hydroxide solution and 4 parts of hydroquinone monomethyl ether were initially placed in a 1 l three-necked flask equipped with a stirrer, a reflux condenser and an electrical thermometer, and were heated to 130° C. with stirring. 198 parts of butanediol diacrylate were metered in in the course of one hour. After a further 2 hours the double bond content was less than 0.2%. The potassium hydroxide solution was then neutralized with methanolic hydrochloric acid. The low-boiling constituents were removed by applying a high vacuum at 100° C. This left 464 parts of a pale yellow, viscous liquid. C—H equivalent weight 232.

(B6) 250 parts of a polyethylene glycol diamine (amine number 243), dissolved in 166 parts of diethylene glycol dimethyl ether, were added dropwise at −20° C. to a solution of 190 parts of diketene in 134 parts of diethylene glycol dimethyl ether. After being stirred for 1½ hours at −28° C., the mixture was warmed to +10° C. and was then stirred until an amine number less than 1 had been reached. After 10 parts of ethanol had been added, the mixture was heated at 90° C. for 40 minutes. The solvent was then removed by vacuum distillation. The residue was taken up in 100 parts of dimethoxyethane. This gave a clear, pale yellow solution. Solids content 81%; C—H equivalent weight 122.

(B7) 134 parts of trimethylolpropane and 327 parts of methyl cyanoacetate were heated with 4 parts of titanium acetylacetonate from 100° to 180° C. with removal of methanol by distillation. After 4 hours, the mixture was cooled to 140° C., and the low-boiling fraction was removed by vacuum distillation. This left 341 parts of a yellow liquid. C—H equivalent weight 57.

(B8) 750 parts of the acrylic resin mentioned under A1 (OH number 150) and 260 parts of ethyl acetoacetate were heated to 150° C. in a distillaton apparatus. The mixture was heated to 170° C. in the course of 2 hours.

When the removal of the ethanol by distillaton was complete, the low boiling fraction was removed by applying a vacuum. After the mixture had been cooled to 100° C., 306 parts of xylene were added. This gave a clear, pale yellow liquid. Solids content 75%; C—H equivalent weight 310.

(B9) 510 parts of a polyester (OH number 110) prepared from trimethylolpropane, terephthalic acid, adipic acid and neopentylglycol were heated to 140° C. with 130 parts of ethyl acetoacetate. The mixture was heated to 170° C. in the course of 3 hours while volatile constituents were continuously removed by distillation. After the residue had been cooled to 140° C., the low-boiling fraction was removed by vacuum distillation. The residue was then diluted with 198 parts of xylene. This gave a clear, pale yellow solution. Solids content 75%; C—H equivalent weight 402.

(B10) 300 parts of the acrylic resin, containing OH groups, mentioned under A1 were dissolved in 200 parts of xylene at 70° C. When the solution had been cooled to room temperature, 0.025 part of dimethylaminopyridine was added. 60 parts of diketene were added dropwise in the course of 6 hours. After a further 12 hours the content of free diketene was 0.2%. Solids content 65%; C—H equivalent weight 392.

(B11) 440 parts of coconut oil fatty acid methyl ester (saponification number 255) and 268 parts of trimethylolpropane and 1 part of butyl titanate were heated to 180° C. in a distillation apparatus. The temperature was slowly increased to 250° C. in the course of 7 hours, with continuous removal of methanol by distillation. After a total of 59 parts of methanol had been distilled off, the mixture was cooled to 100° C., and 585 parts of ethyl acetoacetate were added. After the mixture had been warmed to 140° C., it was heated to 175° C. in the course of 3 hours, with continuous distillation. In total, a further 175 parts of distillate were obtained. After the mixture had been cooled to 150° C., the low-boiling fraction was removed in vacuo. This gave 992 parts of a viscous, pale yellow liquid. C—H equivalent weight 124.

(B12) 200 parts of acetylacetone and 0.5 part of trimethylbenzylammonium hydroxide were warmed to 40° C. 170 parts of trimethylolpropane trisacrylate were added dropwise in the course of 2 hours. The mixture was then stirred until it had a double bond content of less than 0.5%. A pale yellow, viscous liquid was obtained. C—H equivalent weight 162.

(III)

Preparation of a self-crosslinking reaction product in accordance with the invention (C) (Example 17) 924 parts of a 70% strength solution in xylene of an acrylic resin (OH number 130) (carrier substance) prepared by free radical polymerization of styrene, hydroxyethyl methacrylate and methyl methacrylate were reacted, at 40° C., with 258 parts of a 70% strength solution in xylene of a toluylene diisocyanate, half-masked with hydroxyethyl acrylate (N=C=O content 9.8%, C=C equivalent weight 290) (component A), in the presence of 5 parts of dibutyltin dilaurate, until an isocyanate content of less than 0.3% had been reached. 2 parts of dimethylaminopyridine were then added and 25 parts of diketene (component B) were added dropwise at room temperature, with stirring. After stirring at room temperature for 24 hours, free diketene could no longer be detected. Solids content 71%; C=C equivalent weight 2,022; C—H equivalent weight 2,020. The equivalent amount of acetoacetic ester can also be reacted instead of diketene, a product with the same characteristic data being obtained.

(IV)

Preparation of coatings—Examples 1 to 51

Examples 1 to 51 according to the invention are summarized in Tables 1 and 2. In addition, four comparison tests V1 to 4 using commercially available products are also described.

The amounts by weight of the components A and B indicated in Tables 1 and 2 below were mixed. The comparison substance used was a copolymer prepared from 31 parts of glycidyl methacrylate, 15 parts of dimethyl maleate and 54 parts of styrene. The curing agent used for this system was diethylene triamine. In the case of the pigmented coatings, the amount of titanium dioxide corresponding to the desired degree of pigmentation was mixed in, and the mixture was ground on a bead mill. The resulting coating material, as such or, if necessary, after the catalyst indicated had been mixed in, was applied to glass sheets in a wet film thickness of 100 μm by means of a doctor-blade, and was cured at ambient temperature or at 80° C. (30 minutes).

The abbreviations used in the Tables below denote as follows:
ABAH: Alkylbenzyldimethylammonium hydroxide (alkyl=$C_{16}$–$C_{22}$)
BTAH: Benzyltrimethylammonium hydroxide
DETA: Diethylenetriamine
HC: Hot curing=30 minutes at 80° C.
RT: Room temperature
TBAF: Tetrabutylammonium fluoride
TBAH: Tetrabutylammonium hydroxide
TMPSG: Trimethylolpropane trithioglycolate
TMPTA: Trimethylolpropane trisacrylate
TPTP: Tris-p-tolylphosphane
MDPP: Methyl diphenylphosphane
PDOAP: Phenyl di-o-anisylphosphane
DPOAP: Diphenyl-o-anisylphosphane
TPAP: Tris-p-anisylphosphane
MDPAP: Methyl di-p-anisylphosphane
DPPDAPP: Diphenyl-p-dimethylaminophenylphosphane
THMP: Trishydroxymethylphosphane
TCEP: Tris-2-cyanoethylphosphane
TDAMP: Tris diethylaminomethylphosphane
TDAIP: Tris dimethylamino-1,1-dimethylbenzyliminophosphorane
TBIP: Tributyl-1,1-dimethylbenzyliminophosphorane
TPP: Triphenylphosphane
DBU: 1,8-Diazabicyclo-[5.4.0]-undec-7-ene
DBN: 1,5-Diazabicyclo-[4.3.0]-non-5-ene
TMG: N,N,N',N'-tetramethylguanidine
DABCO: 1,4-diazabicyclo-[2.2.2]-octane.

TABLE 1

Clear lacquer film (100μ wet film)

| Example | Component A | | Component B | | Catalyst | | Pot life (hours) | Curing temperature | Konig pendulum hardness (seconds) | | Resistance (after 10 days) to xylene |
|---|---|---|---|---|---|---|---|---|---|---|---|
| | Type | Amount | Type | Amount | Type | Amount | | | After 1 day | After 10 days | |
| 1 | TMPTA | 49 | B 2 | 32 | TBAH | 0.4 | 0.6 | RT | 80 | 170 | >24 hours |
| 2 | A 6 | 88 | B 2 | 32 | BTAH | 0.6 | 0.3 | RT | 157 | 195 | >24 hours |
| 3 | A 6 | 88 | B 2 | 32 | ABAH | 0.6 | 1 | RT | 104 | 140 | >24 hours |
| 4 | TMPTA | 99 | B 6 | 122 | BTAH | 1.0 | 0.25 | RT | 122 | 165 | >24 hours |
| 5 | A 3 | 102 | B 2 | 6.5 | BTAH | 0.6 | 0.3 | RT | 143 | 190 | >24 hours |
| 6 | A 3 | 102 | B 2 | 6.5 | TBAF | 0.6 | 5 | RT | 98 | 202 | >24 hours |
| 7 | TMPTA | 99 | B 8 | 310 | TBAF | 4.0 | 6 | RT | 70 | 104 | 1 hour |
| 8 | A 6 | 88 | B 8 | 310 | TBAF | 4.0 | 8 | RT | 80 | 123 | 1 hour |
| 9 | A 6 | 44 | B 8 | 310 | TBAF | 3.5 | 11 | RT | 160 | 200 | 30 minutes |
| 10 | TMPTA | 74 | B 12 | 40.5 | BTAH | 0.6 | 0.3 | RT | 193 | 206 | >24 hours |
| 11 | A 5 | 12 | B 8 | 22 | TBAH | 0.3 | 0.6 | HC | 169 | 194 | 2 hours |
| 12 | A 3 | 30.7 | TMPSG | 3.6 | TBAF | 0.2 | 0.6 | HC | 191 | 200 | 1 hour |
| 13 | A 3 | 30.7 | DETA | 0.7 | — | — | 0.3 | HC | 151 | 160 | 30 minutes |
| 14 | — | | Type C | 54 | TBAF | 0.3 | 0.4 | RT | 125 | 199 | 2 hours |
| 15 | A 3 | 102 | B 2 | 6.5 | TPP | 0.7 | 28 | RT | 143 | 199 | >24 hours |
| 16 | A 3 | 102 | B 2 | 6.5 | TPTP | 0.4 | 12 | HC | 136 | 217 | >24 hours |
| 17 | A 3 | 102 | B 2 | 6.5 | MDPAP | 0.4 | 10 | HC | 139 | 216 | >24 hours |
| 18 | A 3 | 102 | B 2 | 6.5 | TPAP | 0.4 | 16 | HC | 125 | 210 | >24 hours |
| 19 | A 3 | 102 | B 2 | 6.5 | DBN | 0.2 | 1.5 | RT | 169 | 203 | >24 hours |
| 20 | A 3 | 102 | B 2 | 6.5 | TMG | 0.2 | 1.5 | HC | 196 | 203 | >24 hours |
| 21 | A 3 | 102 | B 2 | 6.5 | MDPP | 0.4 | 11 | HC | 124 | 189 | >24 hours |
| 22 | A 3 | 102 | B 2 | 6.5 | RDOAP | 0.4 | 15 | HC | 136 | 192 | >24 hours |
| 23 | A 3 | 102 | B 2 | 6.5 | DPOAP | 0.4 | 17 | HC | 133 | 196 | >24 hours |
| 24 | A 3 | 102 | B 2 | 6.5 | DPPDAPP | 0.4 | 4.5 | HC | 142 | 202 | >24 hours |
| 25 | A 3 | 102 | B 2 | 6.5 | THMP | 0.4 | 1.5 | RT | 141 | 200 | >24 hours |
| 26 | A 3 | 102 | B 2 | 6.5 | TCEP | 0.4 | 6 | HC | 122 | 201 | >24 hours |
| 27 | A 3 | 102 | B 2 | 6.5 | TDAMP | 0.4 | 16 | HC | 130 | 199 | >24 hours |
| 28 | A 3 | 102 | B 2 | 6.5 | TDAIP | 0.4 | 2.5 | HC | 140 | 202 | >24 hours |
| 29 | A 3 | 102 | B 2 | 6.5 | TBIP | 0.4 | 9 | RT | 140 | 198 | >24 hours |
| 30 | A 3 | 102 | B 3 | 8.0 | TBIP | 0.7 | 12 | HC | 98 | 176 | 14 hours |
| 31 | A 3 | 102 | B 3 | 8.0 | DPPDAPP | 0.7 | 25 | HC | 95 | 172 | 18 hours |
| 32 | A 3 | 102 | B 3 | 8.0 | TDAIP | 0.4 | 8 | HC | 101 | 182 | 12 hours |
| 33 | A 3 | 102 | B 3 | 8.0 | MDPP | 0.7 | 1 | RT | 120 | 193 | >24 hours |
| 34 | A 3 | 102 | B 3 | 8.0 | MDPP | 0.4 | 24 | RT | 104 | 191 | >24 hours |
| 35 | A 3 | 102 | B 3 | 8.0 | DABCO | 0.4 | 5.5 | HC | 145 | 202 | >24 hours |
| 36 | A 3 | 102 | B 3 | 8.0 | TMG | 0.4 | 4.8 | HC | 130 | 207 | >24 hours |
| 37 | A 3 | 102 | B 3 | 8.0 | DBU | 0.4 | 5.5 | HC | 125 | 181 | >24 hours |
| 38 | A 3 | 102 | B 3 | 8.0 | TBAF | 0.8 | 24 | HC | 92 | 179 | 10 hours |
| V1 | (comparison) | 45.8 | DETA | 2.1 | — | — | 24 hours | RT | 65 | 117 | 10 minutes / 20 minutes |
| V2 | (comparison) | 45.8 | DETA | 2.1 | — | — | 24 hours | HC | 132 | 142 | 15 minutes / 50 minutes |

TABLE 2

Pigmented coatings (100μ wet film)

| Example | Component A Type | Component A Amount | Component B Type | Component B Amount | Catalyst Type | Catalyst Amount | TiO₂ | Pot life (hours) | Curing temperature | Konig pendulum hardness (seconds) After 1 day | Konig pendulum hardness (seconds) After 10 days | Resistance (after 10 days) to xylene |
|---|---|---|---|---|---|---|---|---|---|---|---|---|
| 39 | TMPTA | 49 | B 2 | 32 | BTAH | 0.5 | 65.2 | 25 | RT | 131 | 172 | >24 hours |
| 40 | A 6 | 88 | B 2 | 32 | BTAH | 0.9 | 96.5 | 15 | RT | 151 | 171 | >24 hours |
| 41 | A 6 | 88 | B 2 | 32 | TBAF | 1.3 | 96.5 | 35 | RT | 145 | 190 | >24 hours |
| 42 | TMPTA | 49 | B 2 | 32 | TABAF | 0.3 | 65.2 | 30 | RT | 127 | 174 | >24 hours |
|    |       |    |     |    | BTAH | 0.3 |      |    |    |     |     |           |
| 43 | A 5 | 86 | B 2 | 32 | BTAH | 0.8 | 86.5 | 15 | RT | 118 | 162 | >24 hours |
| 44 | A 6 | 44 | B 2 | 32 | TBAF | 1 | 81.2 | 35 | RT | 145 | 175 | 6 hours |
|    | TMPTA | 25 |   |    |      |   |      |    |    |     |     |         |
| 45 | TMPTA | 25 | B 11 | 31 | BTAH | 0.8 | 45 | 20 | RT | 81 | 125 | 30 minutes |
| 46 | TMPTA | 74 | B 12 | 40.5 | BTAH | 1.2 | 91.6 | 45 | RT | 60 | 104 | >24 hours |
| 47 | A 3 | 255.5 | B 2 | 32 | BTAH | 1.4 | 154 | 5 | RT | 126 | 168 | 3 hours |
| 48 | A 3 | 255.5 | B 2 | 32 | TBAF | 1.4 | 154 | 30 | RT | 97 | 174 | >24 hours |
| 49 | A 3 | 128.0 | B 8 | 39 | TBAF | 0.8 | 87 | 40 | RT | 77 | 162 | 8 hours |
| 50 | A 3 | 30.7 | TMPSG | 3.6 | TBAF | 0.4 | 18.2 | 35 | HC | 180 | 182 | 1 hour |
| 51 | A 3 | 30.7 | DETA | 0.7 | — | — | 15.9 | 25 | RT | 140 | 157 | 30 minutes |
| V3 (comparison) | A 3 | 45.8 | DETA | 2.1 | — | — | 38.3 | 16 hours | RT | 55 | 117 | 12 minutes 25 minutes |
| V4 (comparison) | A 3 | 45.8 | DETA | 2.1 | — | — | 38.3 | 16 hours | HC | 138 | 147 | 20 minutes 50 minutes |

(V)

Discussion of the results

As can be seen from Table 1, the products of Examples 1 to 38 display a high resistance to chemicals and a high degree of hardness, i.e. they are completely cross-linked although curing has been carried out in some cases only at room temperature. On the other hand, they also have advantageous pot lives, cf. in particular, Examples 6 to 9, 16–18, 22, 23, 27 and 30. The last-mentioned Examples show that a pot life within the range from 5 to approx. 20 hours can be achieved by suitable choice of catalysts. It is evident from Examples 11 to 13 and also 16, 19–21, 24, 28 and 33 to 37 that high values of hardness are obtained even after 1 day if forced drying is employed (hot curing for 30 minutes at 80° C.).

In comparison with Table 1, Table 2 shows that the pot lives of the pigmented systems are somewhat shorter, but that they are nevertheless adequate for reliable processing. As can be seen from Examples 39 to 49, the films cure completely even at room temperature. The resistance to chemicals of the products according to Table 2 is on average higher than that of the unpigmented systems of Table 1.

Examples 12, 13, 50 and 51 show that the amine and mercapto compounds, as component B, also produce complete curing and good resistance to chemicals in the products, the reaction even being carried out without a catalyst in the case of Examples 13 and 51. The physical data of comparison tests V1 to V4 show a low resistance to xylene and also a less pronounced degree of curing. The products according to the invention are therefore superior to the comparison samples.

We claim:

1. A cured reaction product obtained via the Michael reaction in the presence of at least one catalyst selected from the group consisting of diazabicyclooctane (DABCO), fluorides of quaternary ammonium compounds, on their own or as a mixture with alkyl silicates, amidines, tertiary phosphanes of the formula $P(CH_2-Y)_3$ in which the Ys are identical or different and denote the radical —OH, —CH$_2$CN or —N(Z)$_2$ in which Z is an alkyl radical having 1 to 5 carbon atoms, tertiary phosphanes of the formula $P(R^4,R^5,R^6)$ in which the radicals $R^4$, $R^5$ and $R^6$ denote an alkyl radical having 1 to 12 carbon atoms or a phenyl radical which is unsubstituted or substituted by at least one alkyl, alkoxy or dialkylamino group each of which has 1 to 4 carbon atoms in the alkyl radical, and $R^4$, $R^5$ and $R^6$ are identical or different, but at least one of the radicals represents a phenyl radical, and aminophosphoranes of formula $(R^7,R^8,R^9)P=N-C(R^{10},R^{11},R^{12})$ in which $R^7$, $R^8$ and $R^9$ are identical or different and denote an alkyl radical having 1 to 12 carbon atoms or a phenyl radical which is unsubstituted or substituted by at least one alkyl, alkoxy or dialkylamino group each of which has 1 to 4 carbon atoms in the alkyl radical, and $R^{10}$, $R^{11}$ and $R^{12}$ are identical or different and each represents an alkyl radical having 1 to 5 carbon atoms or a phenyl radical of (A) compounds containing at least two $R^1R^2C=CR^3$—X groups (I) with (B) compounds which contain (a) malonic acid moieties attached by an ester linkage
    (b) at least two groups containing active H atoms of the type —CH or —SH (II) or
    (c) at least one active H atom and at least one group of the type (II), in which, in formula (I), X denotes —CO— which is attached to a further $R^1R^2C=CR^3$ group either directly or via the radical of a polyhydric alcohol or of an amine, $R^1$ denotes hydrogen or a hydrocarbon radical having 1 to 10 carbon atoms, $R^2$ denotes hydrogen, a hydrocarbon radical having 1 to 10 carbon atoms, an ester group containing the radical $R'^4$ of a monohydric alcohol having up to 12 carbon atoms, —CN, —NO$_2$ or a —CO—NHR$^1$ or —CO—R$^1$ group, and $R^3$ has the same meaning as $R^2$ and is identical with or different from the latter.

2. Reaction product as claimed in claim 1, wherein the radical $R^1R^2C=CR^3$—X (I) in the compound (A) is derived from at least one acid selected from the groups consisting of acrylic acid, methacrylic acid, maleic acid and its anhydride and the compound (B) contains malonic acid moieties attached by an ester linkage.

3. Reaction product as claimed in claim 1, wherein the radical $R^1R^2C=CR^3$—X (I) in which X denotes —CO— and $R^3$ denotes hydrogen or alkyl having 1 to 8 carbon atoms, is derived from a monounsaturated or polyunsaturated carboxylic acid having a basicity of not more than two and containing 2 to 10 carbon atoms.

4. Reaction product as claimed in claim 1, wherein the groups (I) in the compounds (A) are attached to an oligomer or polymer.

5. Reaction product as claimed in claim 1, wherein the compound (A) is derived from at least one resin selected from the group consisting of a polyester, an acrylic resin, an epoxide resin each containing OH-groups and amine resin.

6. Reaction product as claimed in claim 1, wherein the group (II) of the compound (B) is derived:

(aa) when it denotes

from a compound containing the grouping —CO—CHR$^1$—CO—, NC—CHR$^1$—CO—, NC—CH$_2$—CN, =PO—CHR$^1$—CO—, =CHR$^1$—CN, =PO—CHR$^1$—PO=, or —CO—CHR$^1$—NO$_2$, and (cc) when it denotes —SH, from at least one component selected from the group consisting of thioalcohol acid ester, amide and a mercaptan.

7. Reaction product as claimed in claim 1, wherein the compound (B) is derived from an at least bifunctional compound selected from the group consisting of polyols, polyamines and polymercaptans.

8. Reaction product as claimed in claim 1, wherein the product is present on a substrate.

9. A process for the preparation of reaction products which comprises reacting via michael reaction compound (A) containing at least two $R^1R^2C=CR^3$—X groups (I) with compound (B) which contains (a) at least two active H atoms or
    (b) at least two groups containing active H atoms of the type —AH— (II) or
    (c) at least one active H atom and at least one group of the type (II), or which form the corresponding amount of this group (II), in which, in formula (I), X denotes —CO— which is attached to a further $R^1R^2C=CR^3$ group either directly or via the radical of a polyhydric alcohol or of an amine, $R^1$ denotes hydrogen or a hydrocarbon radical having 1 to 10 carbon atoms, $R^2$ denotes hydrogen, a hydrocarbon radical having 1 to 10 carbon atoms, an ester group containing the radical $R'^4$ of a monohydric alcohol having up to 12 carbon atoms, —CN, —NO$_2$ or a CO—NHR$^1$ or CO—R$^1$ group, and R$^3$ has the same meaning as R$^2$ and is identical with or different from the latter, and in formula (II), —AH— denotes one of the groupings

—NH— and —SH, under the formation of an oligomeric or polymeric reaction product, the reaction being carried out, in the event that —AH— represents one of the groups

or —SH, in the presence of at least one catalyst selected from the group consisting of diazabicyclooctane (DABCO), halides of quaternary ammonium compounds, on their own or as a mixture with alkyl silicates, amidines, organic phosphonium salts having 1 to 20 carbon atoms in the alkyl radical or aryl radical or both, tertiary phosphanes of the general formula P(CH$_2$—Y)$_3$ in which the Ys are identical or different and denote the radical —OH, —CH$_2$CN or —N(Z)$_2$ in which Z is an alkyl radical having 1 to 5 carbon atoms, tertiary phosphanes of the general formula P(R$^4$,R$^5$,R$^6$) in which the radicals R$^4$, R$^5$ and R$^6$ denote an alkyl radical having 1 to 12 carbon atoms or a phenyl radical which is unsubstituted or substituted by at least one alkyl, alkoxy or dialkylamino group each of which has 1 to 4 carbon atoms in the alkyl radical, and R$^4$, R$^5$ and R$^6$ are identical of different but at least one of the radicals represents a phenyl radical, and aminophosphoranes of the general formula (R$^7$,R$^8$,R$^9$)P=N—C(R$^{10}$,R$^{11}$;R$^{12}$) in which R$^7$, R$^8$ and R$^9$ are identical or different and denote an alkyl radical having 1 to 12 carbon atoms or a phenyl radical which is unsubstituted or substituted by at least one alkyl, alkoxy or dialkylamino group each of which has 1 to 4 carbon atoms in the alkyl radical, and R$^{10}$, R$^{11}$ and R$^{12}$ are identical or different and each represents an alkyl radical having 1 to 5 carbon atoms or a phenyl radical.

10. The process as claimed in claim 9, wherein the catalysts employed are fluorides or phosphanes.

11. The process as claimed in claim 9, wherein the catalysts employed are trishydroxymethylphosphane, trisdimethylaminomethylphosphane, tris-p-anisylphosphane, methyldiphenylphosphane, methyl di-p-anisylphosphane or α,α-dimethylbenzyliminotributylphosphorane.

12. A process as claimed in claim 9, werein the reaction is carried out at a temperature from −10° to 180° C.

13. A process as claimed in claim 9, wherein a component (A) is reacted in which the radical R$^1$R$^2$C=CR$^3$—X (I) in which X denotes —CO— and R$^3$ denotes hydrogen or alkyl having 1 to 8 carbon atoms, is derived from a monounsaturated or polyunsaturated carboxylic acid having a basicity of not more than two and containing 2 to 10, preferably 3 to 6, carbon atoms, preferably acrylic acid, methacrylic acid and/or maleic acid.

14. A process as claimed in claim 9, wherein a compound A is reacted which groups (I) are attached to an oligomer and/or polymer.

15. A process as claimed in claim 9, wherein a compound (A) is reacted which is derived from at least one resin selected from the group consisting of a polyester, an acrylic resin, epoxide resin each containing OH-groups and amine resin.

16. A process as claimed in claim 9, wherein a compound (B) is reacted in which the grouping —AH—(II) is derived (aa) when it denotes

from a compound containing the grouping —CO—CHR$^1$—CO—, NC—CHR$^1$—CO—, NC—CH$_2$—CN, =PO—CHR$^1$—CO—, =CHR$^1$—CN, =PO—CHR$^1$—PO=, or —CO—CHR$^1$—NO$_2$, (bb) when it denotes —NH—, from a primary or secondary polyamine or both and (cc) when it denotes —SH, from at least one component selected from the group consisting of thioalcohol acid ester, amide and a mercaptan.

17. A process as claimed in claim 9, wherein a compound (B) is reacted which is derived from an at least bifunctional compound selected from the group consisting of polyols, polyamines and polymercaptans.

* * * * *